Jan. 1, 1974 G. MERRILL Plant Pat. 3,413
PEACH TREE
Filed Jan. 28, 1971
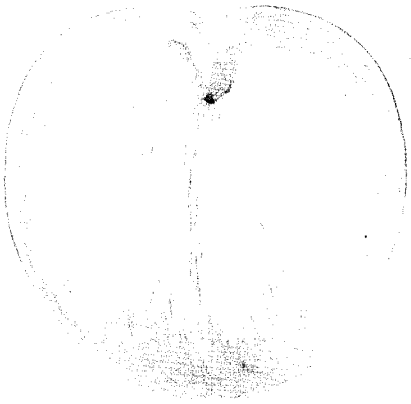
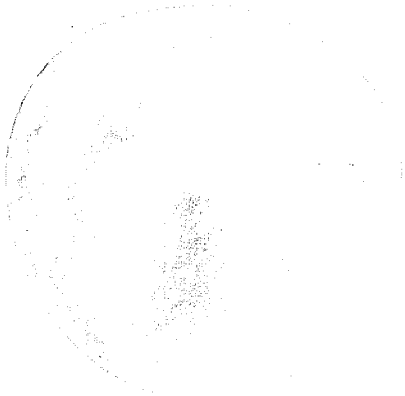
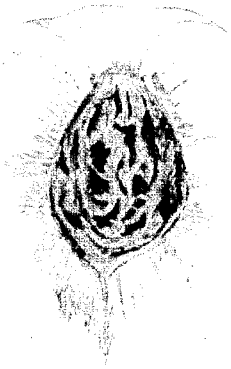
GRANT MERRILL
INVENTOR
Virgil L. Gerard
ATTORNEY

United States Patent Office

Plant Pat. 3,413
Patented Jan. 1, 1974

3,413

PEACH TREE

Grant Merrill, 416 N. Anderson Road,
Exeter, Calif. 93221

Filed Jan. 28, 1971, Ser. No. 110,676
Int. Cl. A01h *5/03*
U.S. Cl. Plt.—43 1 Claim The present invention relates to a peach tree and more particularly to a new and distinct variety thereof broadly characterized by a vigrous tree, regularly producing large, firm fruit with a bright red color over 50% to 75% of its skin surface on average mature trees and a bright yellow undercolor, which matures about two weeks after Rio Oso Gem (U.S. Plant Pat. No. 84), a date at which no other variety of peach so highly colored and regularly producing matures.

The instant variety most clearly resembles Angelus (U.S. Plant Pat. No. 1,966) but is distinguishable therefrom and an improvement thereon by reason of its maturing about three weeks later.

I originated the present variety of peach on a farm formerly owned by me at Red Bluff, Tehama County, Calif., as follows: I crossed a J. H. Hale (unpatented) with a third generation open pollinated seedling of a cross of J. H. Hale with Levi Cling (unpatented). A resultant seedling thus produced, numbered E8–7W for reference purposes, which is the instant variety, was then asexually reproduced by budding onto a small tree which I then transplanted to my farm at Exeter, Tulare County, Calif. The instant variety was then grafted onto a tree on a farm at Dinuba, Tulare County, Calif. In each case, the fruit and tree characteristics remained the same as those of the original fruit and tree (seedling E8–7W) and proved worthy of commercial use.

The accompanying drawing is an oil painting of a characteristic mature fruit of the subject peach variety showing the shape and skin color, and by means of a fruit divided on its suture plane, showing the flesh and stone color and the freedom of the flesh from the stone in a mature fruit.

Referring now more specifically to the pomological characteristics of this new and distinct variety of peach tree, the following is an outline description thereof observed under the ecological conditions prevailing in Tulare County, Calif. All major color plate identifications are by reference to Maerz and Paul's Dictionary of Color, First Edition.

TREE

Generally: medium size, vigor and density; may be pruned to vase shape.
Productivity: heavy bearer, sets fruit regularly.
Trunk: straight, medium stocky, shaggy and gray.
Branches: gray on older branches, brown when young, straight with some bending.
Lenticels: medium in quantity and size.
Twigs: medium size with medium internode length; current season's growth, green; older growth, brown.

LEAVES

Shape: lanceolate, tip accuminate.
Size: medium to large; 5 to 7 inches long, 1⅜ to 2 inches wide taken at center portion of new growth 18 to 30 inches long; medium thick.
Color: dark green upper surface, medium green lower surface, light yellowish green veins on the under surface.
Class: Meader and Blake: Proceedings of the American Society for Horticultural Science, Volume 37, page 203—Class 3.
Margin: crenate.
Petiole: generally about ⅜ inch long.
Glands: reniform.

FLOWERS

Buds: medium size, free, plump, pubescent.
Blooms: large, showy, pink.
Date of bloom: early to mid-season, about with Fiesta (U.S. Plant Pat. No. 1,099).
Pollen: abundant.

FRUIT (described at maturity)

Season of ripening: about three weeks later than Angelus (U.S. Plant Pat. No. 1,966), about two weeks later than Rio Oso Gem (U.S. Plant Pat. No. 84), and about with or slightly later than Merricle L–120 (U.S. Plant Pat. No. 2,071).
Size and shape: generally very large; generally globose but variable; axial diameter, 2⅜ to 3¼ inches; transverse in suture plane, 2½ to 3¼ inches; and at right angle to suture plane, 2⅜ to 3⅛ inches.
Suture: shallow, extends from base but discontinues at apex, a few have a deep suture ¼ to ¾ inches long at the stem end; slight depression beyond pistil point.
Dorsal surface: rounded.
Cavity: medium size, elongated in suture plane; depth, ⅜ to ⅝ inches; width, ½ to 1 inch; color, the same as skin, showing red where exposed to sun.
Base: retuse to emarginate.
Apex: retuse; pistil point, apical, 1/16 to ¼ inch long.
Stem: about ⅛ to ¼ inch long, ⅛ inch in diameter.
Skin color: undercolor, lightest "Golden Glow" 9–L–6 to medium "Forsythia" yellow 9–K–9, with 50% to 75% of the surface an average mature tree covered with "Brigand" red 2–J–11 to "Cardinal" 5–L–6.
Skin thickness: medium.
Skin pubescense: scant.

*Flesh*

Color: yellow "Ta-Ming" 10–L–6, with red in flesh near pit "Chianti" 6–L–6.
Amygdalin: moderate.
Juice: moderate.
Texture: firm.
Fibers: moderate, tender.
Ripens; evenly.
Flavor: mild subacid.
Firmness: generally firm throughout, more pronounced near surface.
Aroma: distinct.
Eating quality: good.

*Stone*

Color: when freshly cut, lightest part "Hyacinth Red" 4–F–11; darkest portion, very dark brown 48–L–12.
Tenacity to flesh: completely free.
Size: medium; length, 1⅜ to 1⅝; width, 1⅛ to 1¼ inches, thickness ¾ to ⅞ inch.
Fibers: short.
Form: obovate, tip cuspidate; base, mostly straight; hilum, oval; sides, mostly equal.
Surface: irregularly furrowed surface most pronounced on the edges, pitted mostly near the center portion of the stone.
Ventral edge: many small grooves with deeper grooves on each side;
Dorsal edge: deep grooves usually along entire length, some only part of length.
Tendency to split: slight.

USE

Shipping quality: good.

Having thus described and illustrated my new variety of peach tree, what is claimed is:

1. A new and distinct variety of peach tree substantially as illustrated and described; being particularly characterized by a vigorously growing, regularly and heavily bearing tree, with fruit that is firm and large, has a bright red skin color over 50% to 75% of its surface and a bright yellow undercolor, and ripening about two weeks after Rio Oso Gem (U.S. Plant Pat. No. 84); and most nearly resembling the Angelus (U.S. Plant Pat. No. 1,966), but being an improvement thereon in ripening about three weeks later.

No references cited.

ROBERT E. BAGWELL, Primary Examiner